(12) United States Patent
Nokes, Jr. et al.

(10) Patent No.: US 9,656,044 B2
(45) Date of Patent: May 23, 2017

(54) CONDUIT MANAGEMENT DEVICE

(71) Applicant: REDpoint International, Inc., Vancouver, WA (US)

(72) Inventors: Charles E. Nokes, Jr., Vancouver, WA (US); Ronald C. Ames, Vancouver, WA (US)

(73) Assignee: REDpoint International Inc., Vancouver, WA (US)

( * ) Notice: Subject to any disclaimer, the term of this patent is extended or adjusted under 35 U.S.C. 154(b) by 0 days.

(21) Appl. No.: 14/198,336

(22) Filed: Mar. 5, 2014

(65) Prior Publication Data

US 2014/0207072 A1    Jul. 24, 2014

Related U.S. Application Data

(63) Continuation-in-part of application No. 13/439,756, filed on Apr. 4, 2012, now abandoned, which is a continuation-in-part of application No. 12/362,404, filed on Jan. 29, 2009, now abandoned.

(51) Int. Cl.
*A61M 25/02* (2006.01)
*A61J 15/00* (2006.01)

(52) U.S. Cl.
CPC .......... *A61M 25/02* (2013.01); *A61J 15/0061* (2013.01); *A61M 2025/0206* (2013.01); *A61M 2025/026* (2013.01); *A61M 2025/0213* (2013.01); *A61M 2025/0253* (2013.01)

(58) Field of Classification Search
CPC .......... A61M 25/02; A61M 2025/0206; A61M 2025/0213; A61M 2025/0233; A61M 2025/0253; A61M 3/027; A61M 16/0683; A61M 2025/0246; A61M 2025/026
See application file for complete search history.

(56) References Cited

U.S. PATENT DOCUMENTS

| | | | |
|---|---|---|---|
| 3,782,378 A * | 1/1974 | Page | 128/888 |
| 3,812,851 A | 5/1974 | Rodriguez | |
| 4,087,864 A | 5/1978 | LaBove et al. | |
| 4,453,933 A | 6/1984 | Speaker | |
| 4,517,971 A * | 5/1985 | Sorbonne | A61M 25/02 128/879 |
| 4,585,443 A | 4/1986 | Kaufman | |

(Continued)

OTHER PUBLICATIONS

Joint Stabilization, Journal of Infusion Nursing, vol. 34, No. 1S, Jan./Feb. 2011, pp. S47-S48.

(Continued)

*Primary Examiner* — Bhisma Mehta
*Assistant Examiner* — Nilay Shah
(74) *Attorney, Agent, or Firm* — Chernoff, Vilhauer, McClung & Stenzel, LLP

(57) ABSTRACT

A conduit management device and method for quickly and easily securing a conduit and reducing the risk of conduit disruption is disclosed. A selectively securable cleat is arranged for selective encirclement and securement of at least a portion of a conduit by wrapping the conduit around the cleat. An embodiment is disclosed having an elongate cleat that is fixed to the patient apparatus at a first location of the cleat spaced apart from releasably securable locations proximate first and second ends of the cleat such that the fixation point at the first location forms the fixed base of the cleat.

1 Claim, 3 Drawing Sheets

(56) References Cited

U.S. PATENT DOCUMENTS

| | | |
|---|---|---|
| 4,671,787 A | 6/1987 | Widman |
| 4,846,807 A | 7/1989 | Safadago |
| 4,919,150 A | 4/1990 | Grant |
| 4,919,654 A * | 4/1990 | Kalt .................... A61M 25/02 128/DIG. 26 |
| 5,018,534 A | 5/1991 | Grant |
| 5,188,608 A | 2/1993 | Fritts |
| 5,190,530 A | 3/1993 | Greeff et al. |
| 5,342,317 A | 8/1994 | Claywell |
| 5,413,120 A | 5/1995 | Grant |
| 5,577,516 A | 11/1996 | Schaeffer |
| 5,682,905 A | 11/1997 | Grant |
| 5,755,698 A * | 5/1998 | Kagan et al. ................. 604/179 |
| 5,916,199 A | 6/1999 | Miles |
| 5,953,752 A | 9/1999 | Jones |
| 6,520,940 B1 | 2/2003 | Gomez |
| D541,934 S | 5/2007 | Gomez |
| 7,284,729 B2 | 10/2007 | Walsh et al. |
| 7,284,730 B2 | 10/2007 | Walsh et al. |
| 7,425,206 B2 | 9/2008 | Byrne et al. |
| 8,123,681 B2 | 2/2012 | Schaeffer |
| 2005/0234423 A1 | 10/2005 | Mogensen |
| 2008/0071224 A1 | 3/2008 | Forsyth |
| 2009/0281502 A1* | 11/2009 | Heitkamp ............. A61M 25/02 604/179 |

OTHER PUBLICATIONS

Vascular Access Device Stabilization, Journal of Infusion Nursing, vol. 34, No. 1S, Jan./Feb. 2011, pp. S46-S47.

* cited by examiner

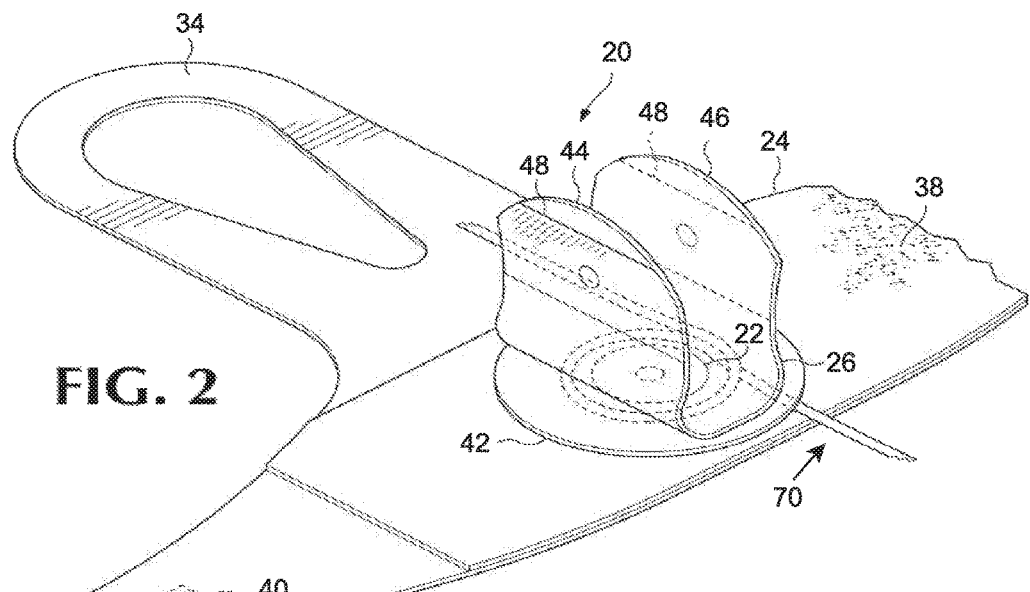
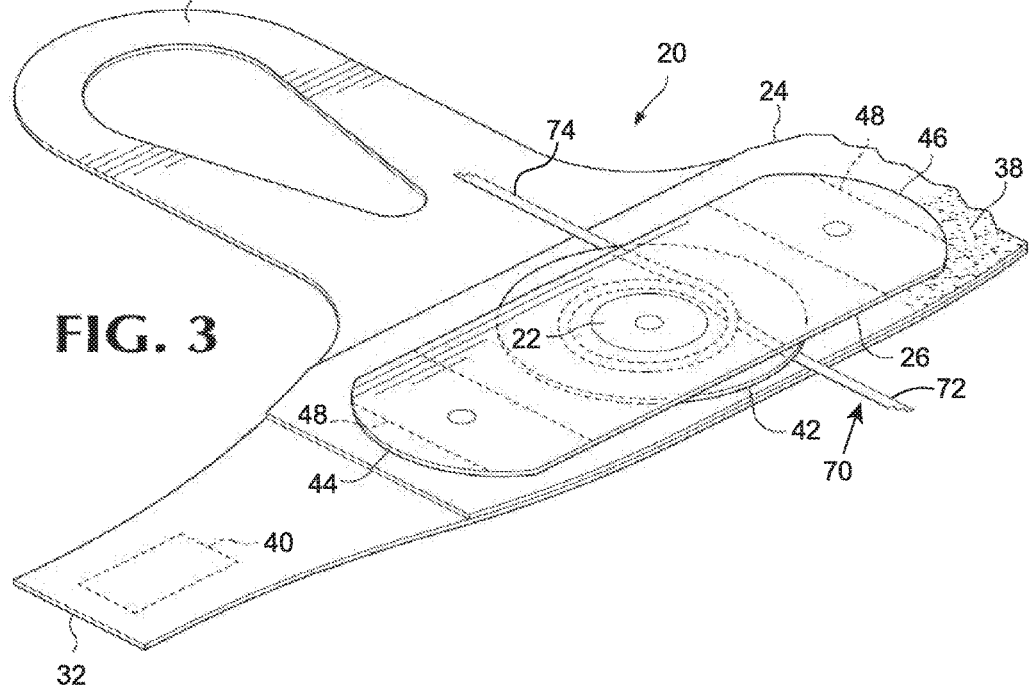

\* Summary of Product trials for 10,164 Patients: Comparing an Intravenous Stabilizing Device to Tape, Gregory J. Schears, Journal of Infusion Nursing, Vol. 29, No. 4, July/August 2006

\*\* Stedline Conduit Management Device test conducted at REDpoint International, 2012

CONDUIT MANAGEMENT DEVICE

CROSS-REFERENCE TO RELATED APPLICATIONS

This application is a continuation-in-part of prior application Ser. No. 13/439,756, filed Apr. 4, 2012 and prior application Ser. No. 12/362,404 filed Jan. 29, 2009.

BACKGROUND OF THE INVENTION

The present invention relates to a device for managing conduits.

Patients with both minor and major illness and injury are often faced with using one or more conduits, such as intravenous (IV) lines, central venous access devices (CVAD), perenteral nutrition (PN) tubes, peripherally inserted central catheter (PICC) lines, elimination tubes, chest tubes, arterial lines, mechanical ventilator tubing, drain tubes and all other catheters, as well as electronic, electrocardiogram (ECG), and other types of biosensor wires.

Many patients are anxious about maintaining their conduit(s). Disruption of a patient's conduit can lead to one or more complications. For example, disruption of a patient's conduit can cause: pain; trauma to the surrounding tissue; prolonged healing time; scarring; readjustment of the conduit; replacement of the conduit; infection; interruption of medical practitioners' access to patient information; interruption of patient access to fluids; prolonged hospitalization; and even death.

Disruption of a patient's conduit can also cause accidental exposure to patient fluid and transmittable disease.

Patients with one or more internal access conduits (IACs), such as IV lines or PN tubes, are at risk for infection, which can lead to serious complications such as prolonged hospitalization or death. It is critically important to maintain all IACs with an eye towards preventing infection. Even greater watchfulness is warranted when caring for patients who are at increased risk of developing infection, including: immunocompromised patients (e.g., oncology patients, HIV+ patients, patients receiving long-term steroids), patients with one or more other infections, patients receiving PN, and patients with multiple IACs.

IAC-related infections occur in several different ways, including: contamination of an IAC or associated device by skin flora on insertion; migration down a cannula tract from the skin; contamination of an IAC or associated device during manipulation; or seeding from another site of infection. Rarely, a contaminated infusate may be the culprit.

Practitioners need to assess the TAC insertion site for many symptoms, including drainage, edema, color, and temperature changes, but such assessment is made more difficult when the patient has suffered or fears suffering unintentional IAC disruptions.

Conventional means of minimizing the risk of IAC-related infections include proper hand-washing by healthcare personnel, using maximal sterile barriers at the time of insertion, use of chlorhexidine gluconate (CHG)-based skin preparations for insertion and care, careful site insertion selection, frequent inspection to review whether IACs are still necessary, and removing IACs as soon as they are no longer necessary. For additional protection against IAC infections, some facilities use CHG-impregnated sponges at the IAC exit site.

Standards of practice regarding CVADs further recommend the use of a manufactured catheter stabilization device specifically engineered to prevent catheter movement into or out of the insertion site. If CVADs are not sutured in place (a practice associated with additional sources of infection), some securement method must be employed.

Frequently, a patient who must have a conduit in place for an extended period of time may be further compromised by limited mobility, cognitive ability, or coordination. Pediatric patients and patients with cognitive deficits may not understand the need to protect the conduit and may need to be physically restrained to prevent conduit disruption.

Patients in transport, particularly emergency transport, run a significant risk of conduit disruption.

To date, known conduit management devices do not provide a quick, easy, and low-risk way to secure the conduit. Known conduit management devices fail: to permit assessment of an IAC insertion site without risk of disrupting the IAC; to permit assessment of a conduit, including at the site of a conduit management device, without risk of disrupting conduit flow; to keep the conduit secure, even if the conduit is subjected to more than 1.5 pounds of pull; to minimize the steps required to secure the conduit; to permit quick and painless removal of the conduit; to provide a convenient, durable, and easy-to-use device for securing the conduit; to minimize unnecessary and hazardous slack in the conduit; to minimize risk of disrupting the conduit; and to minimize risk of severing the conduit. For example, one conduit stabilization device includes one or more male-female connector snaps that risk disrupting conduit flow or severing the conduit.

There is a need for a conduit management device that allows assessment of an IAC insertion site without risk of disrupting the IAC.

There is a need for a conduit management device that allows assessment of a conduit, including at the site of a conduit management device, without risk of disrupting the conduit.

There is a need for a conduit management device that keeps the conduit secure when the conduit is accidentally pulled or tugged, even if the conduit is subjected to more than 1.5 pounds of pull, and whether used in conjunction with known stabilization methods or not.

There is a need for a conduit management device that minimizes the steps required to secure the conduit.

There is a need for a conduit management device that permits quick and painless removal of the conduit.

There is a need for a conduit management device that is convenient, durable, and easy to use, allowing practitioners to incorporate the device into their standard practices for best patient care.

There is a need for a conduit management device that reduces unnecessary and hazardous slack in the conduit.

There is a need for a conduit management device that minimizes risk of disrupting the conduit.

There is a need for a conduit management device that minimizes risk of severing the conduit.

What is desired therefore is a conduit management device that is easy to use, avoids patient exposure to adhesive, secures the conduit against dislodging, and facilitates assessment of the conduit insertion site.

BRIEF DESCRIPTION OF THE SEVERAL VIEWS OF THE DRAWINGS

FIG. 2 is a perspective view of a portion of the exemplary conduit management device of FIG. 1 with the ends of the flap raised to reveal a conduit wrapped around the cleat.

FIG. 3 is a perspective view of a portion of the exemplary conduit management device of FIG. 1 and a conduit secured by the cleat.

DETAILED DESCRIPTION OF PREFERRED EMBODIMENT

The device involves providing an apparatus for a patient, such as a securable dressing or a bed. An elongate cleat is fixed to the patient apparatus at a first location of the cleat spaced apart from a first end of the cleat such that the fixation point at the first location forms the fixed base of the cleat. The fixed base of the cleat is preferably also spaced apart from a second end of the cleat. The cleat is preferably releasably securable to the apparatus at a location proximate the first end. The cleat is preferably also releasable securable to the apparatus at a location proximate the second end. A releasably secure location is preferably secured with a hook and loop fastener such as Velcro® or a similar product. A releasably securable location may instead be secured with a clasp, latch, snap, buckle, or other securing means. A retention washer is preferably wrapped around the fixed cleat base. Use of the device further involves cleating at least a portion of a body conduit by wrapping the body conduit around the fixed base of the cleat. If there is a releasably securable location, it is not secured at the time of cleating, but after cleating, the releasably securable location is secured. Use of this device retains the conduit at the cleat and decreases the risk of conduit disruptions.

A conduit cleat may be of a size to retain a single small or large conduit, or of a size to retain multiple conduits of small, large, or varying sizes.

A fixed cleat base is of a size to prevent disruption of a conduit when the conduit is wrapped around the fixed location.

Use of this device may involve providing known securement devices to assist in managing the conduit.

In the preferred embodiment, the conduit cleat is largely made of a lightweight FDA-approved material.

The device is capable of keeping the conduit secure even when the conduit is subjected to up to 15 pounds or more of pull.

Figure 1:
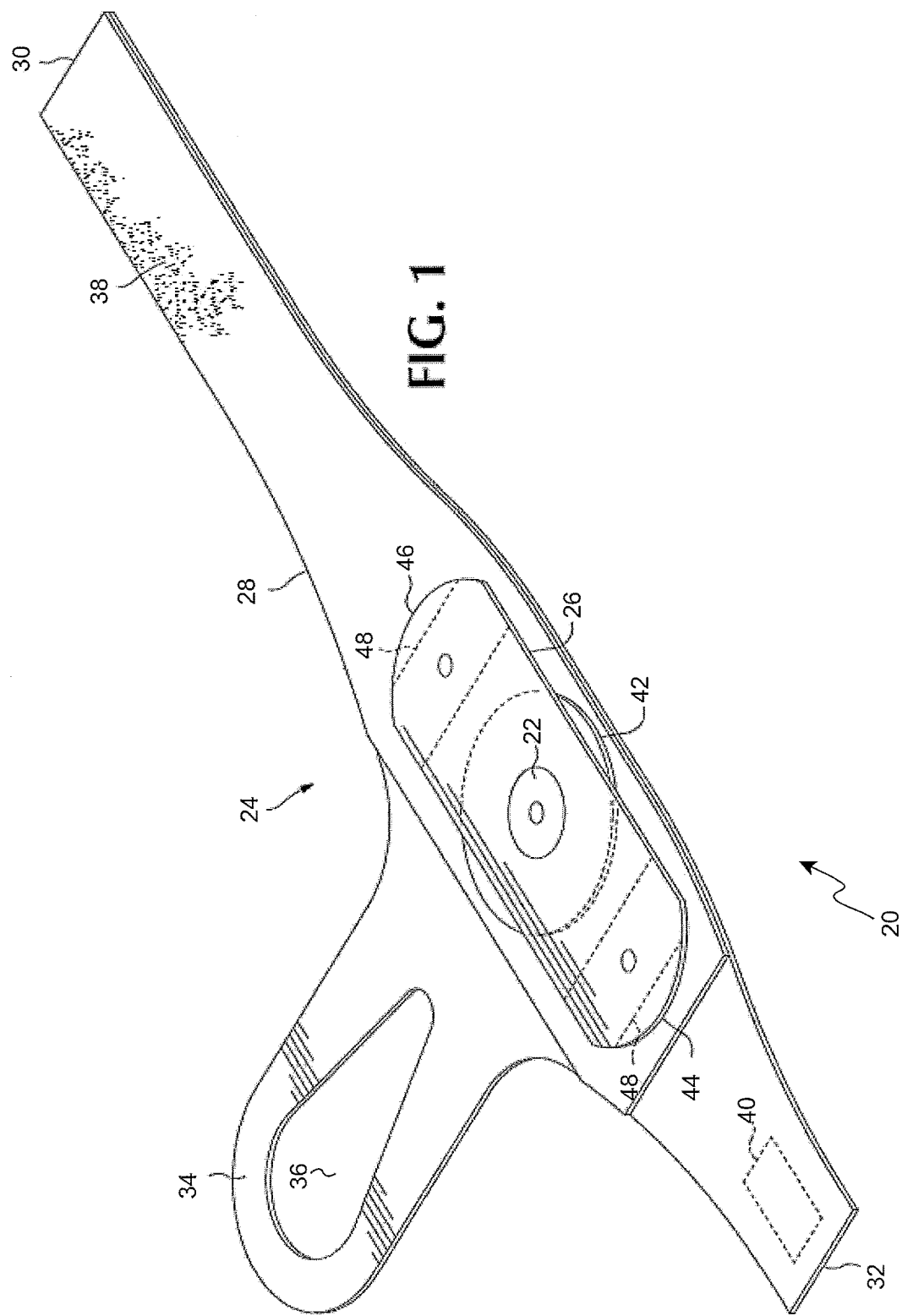
FIG. 1 is a perspective view of an exemplary conduit management device.

Referring to FIGS. 1,2, and 3, a conduit management device 20 comprises, generally, cleat 22 selectively securable to a patient's limb or another object and around which a conduit can be wrapped and secured. The cleat 22 comprises generally a portion of a flexible sleeve 24 which is affixed relative to a portion of an elongate flexible flap 26, at a first portion of the sleeve. The sleeve 24 preferably comprises an elongate first portion 28 having a first end 30 and a second end 32 and a second portion 34 projecting approximately normal to the first portion and defining an aperture 36. The conduit management device 20 can be secured to a patient's limb or another object by wrapping the sleeve 24 around the limb or object and securing the sleeve with cooperating fastening elements 38, 40 including portion proximate, respectively, the first end 30 and the second end 32 of sleeve portion.

Preferably, one of the fastening elements 38 comprises a first element of a hook and loop fastener, for example, a loop portion of a Velcro® hook and loop fastener, attached to a surface of the sleeve 24 and extending, from proximate the first end 30 of the sleeve's elongate first portion 28 a distance toward the second end 32 of the sleeve's first portion. Preferably, the second fastening element 40 is a cooperating second element of a hook and loop fastener affixed to the surface of the sleeve opposite of the surface supporting the element 38 and proximate the second end of the sleeve's first portion. By overlapping the ends of the first portion of the sleeve and securing the hook and loop fastener, the length of the portion of the sleeve encircling a patient's limb or another object can be adjusted to securely fit the encircled limb or object. Other fastening elements such as a buckle, snap, clasp, or other fastening elements could be used to secure the ends of the sleeve. Passing a patient's thumb or another digit through the aperture 36 in the second portion 34 of the sleeve and securing the sleeve in encirclement of the wrist restrains the conduit management device 20 against rotation about the arm.

Preferably a resilient disk 42 is arranged between and affixed to facing surfaces of the sleeve 24 and the flap 26. Preferably, the disk 42 is secured to the sleeve and the flap by riveting, adhesion, welding, or another process which fuses, adheres, or otherwise holds the respective adjoining surfaces fast over an area corresponding to substantial portions of the respective surfaces of the disk, thereby securing a portion of the sleeve relative to a portion of the flap. Preferably, the diameter of the adhered area, the cleat 22, is at least 30% of the diameter of the disk 42 and not greater than 70% of the diameter of the disk. When a conduit 70 is restrained in the conduit management device 20, it is preferably wrapped around the circumference of the fused area, the cleat 22, and, more preferably, wrapped around the circumference of the disk 42, to avoid kinking and interference with passage of fluid through the conduit. Such a conduit 70 has a diameter that is greater than the height of the cleat 22.

The elongate flexible flap 26 is affixed to the disk 42 at a location distal of the flap's ends 44, 46 which are selectively securable to the sleeve, otherwise referred to as second positions. Although other fasteners could be used to releasably secure the end portions of the flap to the sleeve, preferably, flap fastening elements 48 comprising a portion of the cooperating second portion of a hook and loop fastener are secured to the surface of the flap facing the sleeve 24 proximate each end of the flap. The end portions of the flaps are selectively securable by engagement of the fastening elements 48 with portions of the first portion of the hook and loop fastener 38 on the facing surface of the sleeve.

A conduit 70 can be secured in the conduit management device 20 by releasing the ends of the flap 26 and folding the ends of the flap away from sleeve as illustrated in FIG. 2. The conduit can then be laid on the surface of the sleeve 24 and wrapped around the cleat 22. The ends of the flap are then engaged with the sleeve to secure the conduit between the opposing surfaces of the flap and sleeve and in encirclement of the cleat 22. If tension is applied to the conduit on one side of the cleat 22, for example conduit portion 72, friction between the cleat and the conduit limits the transmission of force to and movement of the portion 74 of the conduit on the other side of the cleat.

Figure 4:
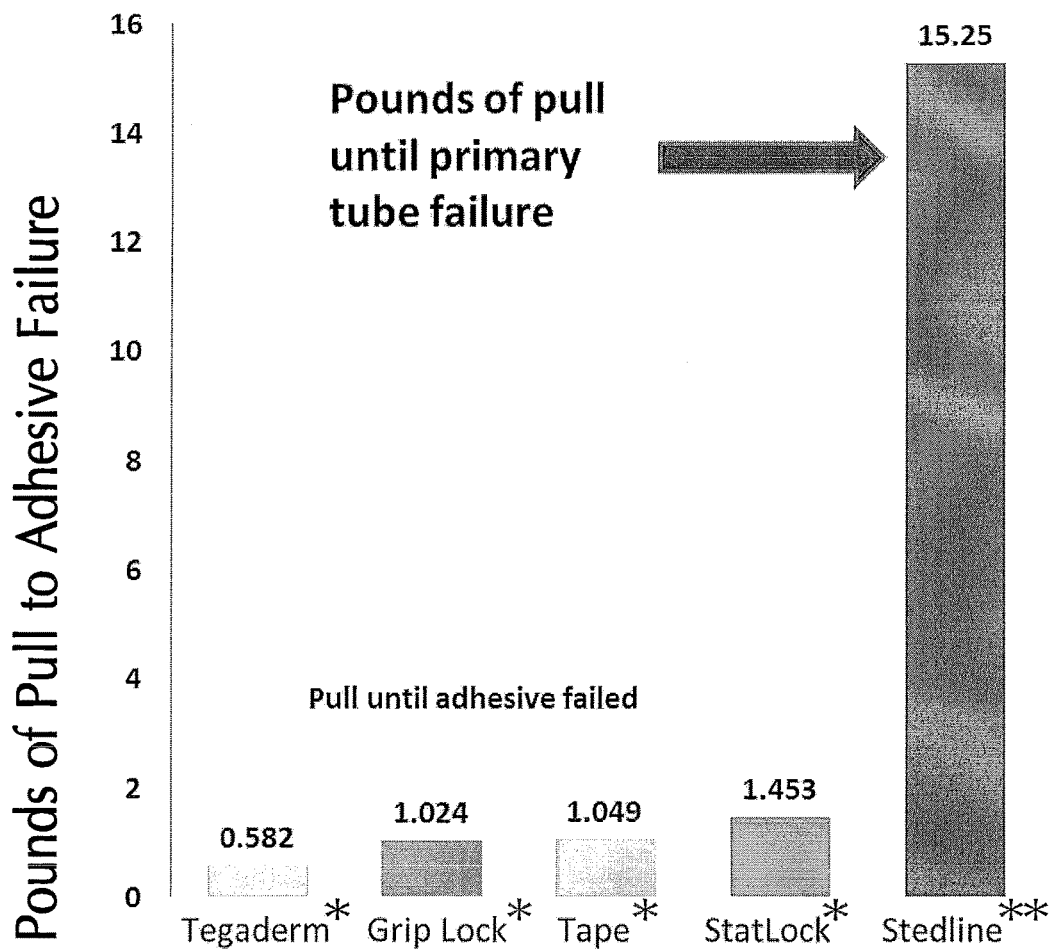
FIG. 4 is a table depicting comparative pull test data for the exemplary embodiment of FIG. 1, labeled the Stedline® device, and for other known conduit management devices.

In testing, an embodiment of this disclosure demonstrated dramatically improved resistance to pressure compared to other known devices. These test results are summarized in FIG. 4 depicting comparative pull test data for an embodiment, labeled the Stedline® device, and for other known conduit management devices. The embodiment withstood more than 15 pounds of pull. Upper ranges of pressure resulted in failure of the conduit line, rather than failure of the embodiment being tested.

The terms and expressions which have been employed in the foregoing specification are used therein as terms of description and not of limitation, and there is no intention, in the use of such terms and expressions, of excluding equivalents of the features shown and described or portions thereof, it being recognized that the scope of the invention is defined and limited only by the claims that follow.

We claim:

1. A conduit management device for effectively securing a conduit to a patient without the use of adhesives, comprising:
   (a) an elongate flexible sleeve having at least two sides, wherein both sides are free from a skin-adhering adhesive, and constructed for encirclement of a body extremity;
   (b) a disc having a first face and a second face and a disc diameter; and
   (c) a thin cleat having a first surface, a second surface, a cleat height, and a cleat diameter, such that said cleat diameter is less than said disc diameter, wherein said first surface is affixed to a first side of said flexible sleeve, and said second surface is affixed to said first face of said disc; such that a space created by said first side of said flexible sleeve, said cleat height and said first face of said disc provides a space and surfaces for selective frictional engagement of a conduit, by selective encirclement of said conduit around said cleat.

* * * * *

UNITED STATES PATENT AND TRADEMARK OFFICE
CERTIFICATE OF CORRECTION

| | | |
|---|---|---|
| PATENT NO. | : 9,656,044 B2 | Page 1 of 1 |
| APPLICATION NO. | : 14/198336 | |
| DATED | : May 23, 2017 | |
| INVENTOR(S) | : Charles E. Nokes et al. | |

It is certified that error appears in the above-identified patent and that said Letters Patent is hereby corrected as shown below:

In the Specification

Column 1, Line 51     "Practitioners need to assess the TAC insertion site..."
should be -- Practitioners need to assess the IAC insertion site... --

Signed and Sealed this
Eleventh Day of July, 2017

Joseph Matal
*Performing the Functions and Duties of the*
*Under Secretary of Commerce for Intellectual Property and*
*Director of the United States Patent and Trademark Office*